(12) United States Patent
Bastia

(10) Patent No.: US 8,303,605 B2
(45) Date of Patent: Nov. 6, 2012

(54) DEVICE FOR ELASTIC LIGATURE OF TISSUES

(75) Inventor: Filippo Bastia, Carpi (IT)

(73) Assignee: THD S.p.A., Correggio (IT)

( * ) Notice: Subject to any disclaimer, the term of this patent is extended or adjusted under 35 U.S.C. 154(b) by 219 days.

(21) Appl. No.: 12/716,909

(22) Filed: Mar. 3, 2010

(65) Prior Publication Data
US 2010/0234859 A1  Sep. 16, 2010

(30) Foreign Application Priority Data

Mar. 12, 2009 (IT) .............................. RE2009A0022

(51) Int. Cl.
*A61B 17/10* (2006.01)
(52) U.S. Cl. ...................................................... 606/140
(58) Field of Classification Search .................. 606/139, 606/140, 141, 142; 128/831
See application file for complete search history.

(56) References Cited

U.S. PATENT DOCUMENTS

| 3,382,873 A | 5/1968 | Banich et al. |
| 3,760,810 A * | 9/1973 | Van Hoorn ..................... 606/140 |
| 7,722,627 B2 * | 5/2010 | Andreen ........................ 606/140 |

FOREIGN PATENT DOCUMENTS

| DE | 198 34 263 A1 | 2/2000 |
| EP | 1 155 660 A1 | 11/2001 |

* cited by examiner

*Primary Examiner* — Julian Woo
(74) *Attorney, Agent, or Firm* — Pearne & Gordon LLP

(57) ABSTRACT

A device for elastic ligature of tissues comprises: a first and a second element, one of which exhibits a support portion for at least a rubber ring, the elements being slidably coupled to one another such that a reciprocal sliding between the elements determines a release of a rubber ring from the support portion; a trigger, manually maneuverable by an operator and acting on at least the second element for realizing a reciprocal sliding between the elements; a connecting portion, connected to the trigger and to the second element and being elastically deformable in order to enable a reciprocal change of orientation between the trigger and the second element.

8 Claims, 3 Drawing Sheets

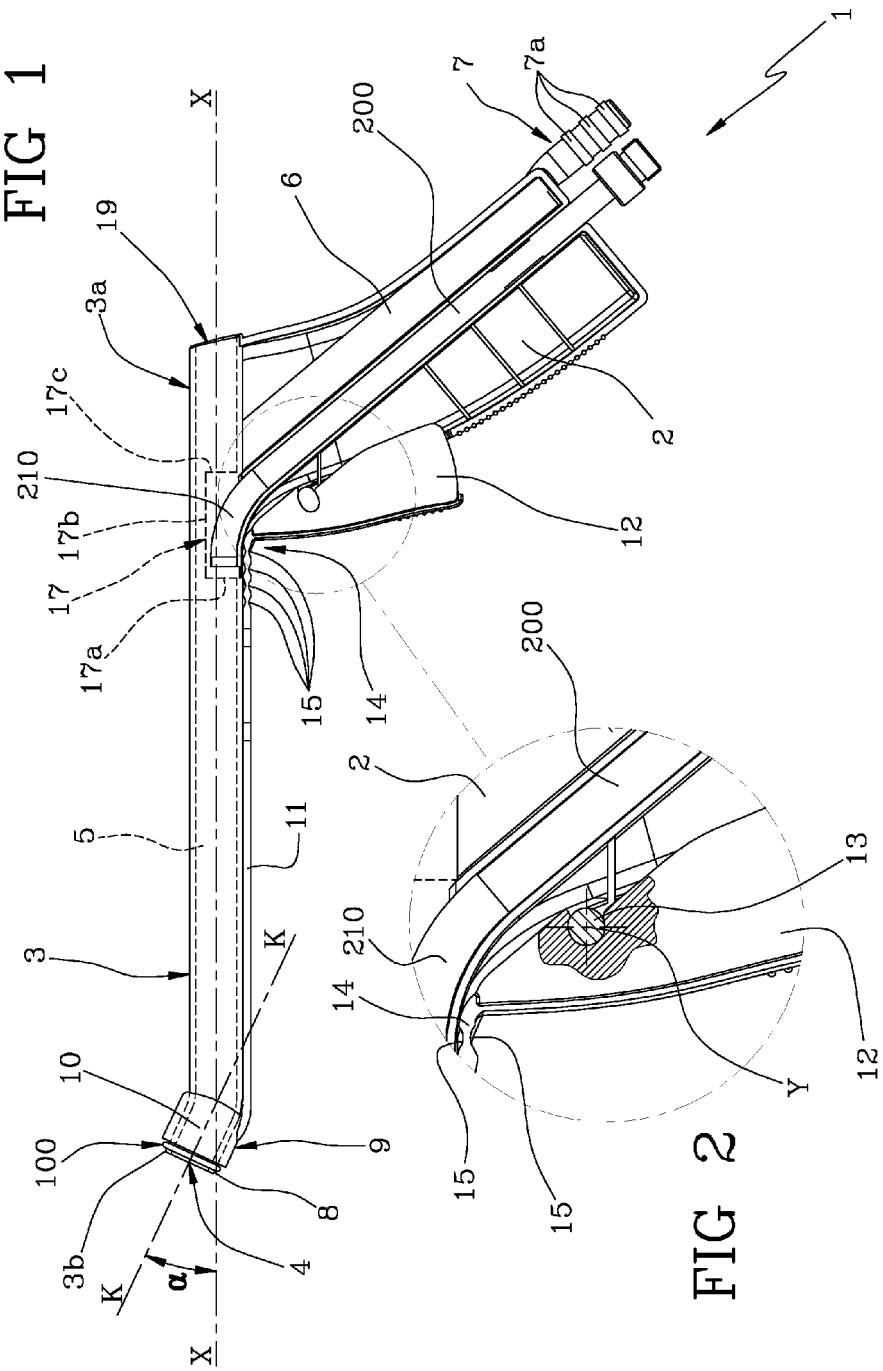

DEVICE FOR ELASTIC LIGATURE OF TISSUES

BACKGROUND OF THE INVENTION

The invention relates to a device for elastic ligature of tissues, and is particularly applicable in treatment of hemorrhoids.

Devices are known which release rubber rings, and comprise a command tube connected to a maneuvering handle and support one or more rubber rings to be released.

The command tube comprises an internal tube on a free end of which the rubber ring is predisposed, and an external tube moved in advancement with respect to the internal tube in order to determine release of the rubber ring. The handle is fixed to the internal tube and exhibits a trigger which can be manually activated by an operator in order to command the advancement of the external tube.

Devices of the above-described type exhibit some complicated aspects, mainly regarding the handle and in connection with the mechanical transmission between the movement of the trigger and the advancing of the external tube. The mechanical transmission is included internally of the handle and exhibits mechanisms and return elements which transform a rotational movement of the trigger into a translational movement of the external tube.

It is also commonly known that devices for treatment of the human body must usually be of the single-use type, due to the sterilization requirements of the devices themselves.

The foregoing demonstrates that known-type devices are poorly adapted to single-use modalities, as they are complex and expensive.

In this context, the technical objective underlying the present invention is to provide a device for elastic ligature of tissues which obviates the drawbacks in the prior art as cited herein above.

In particular, the present invention aims to make available a device for elastically legating tissues which exhibits great constructional simplicity.

A further aim of the present invention is to provide a device for elastic ligature of tissues which exhibits contained manufacturing costs.

The set technical objective and the set aims are substantially attained by a device for elastic ligature of tissues comprising the technical characteristics set out in one or more of the accompanying claims.

BRIEF DESCRIPTION OF THE DRAWINGS

Further characteristics and advantages of the present invention will better emerge from the following non-limiting description of a preferred but not exclusive description of a device for elastic ligature of tissues, as illustrated in the accompanying figures of the drawings, in which:

FIG. 1 is a lateral view of a device of the present invention;

FIG. 2 is an enlarged lateral and partly-sectioned view of a detail of the device of FIG. 1;

DESCRIPTION OF THE PREFERRED EMBODIMENTS

Figure 3:
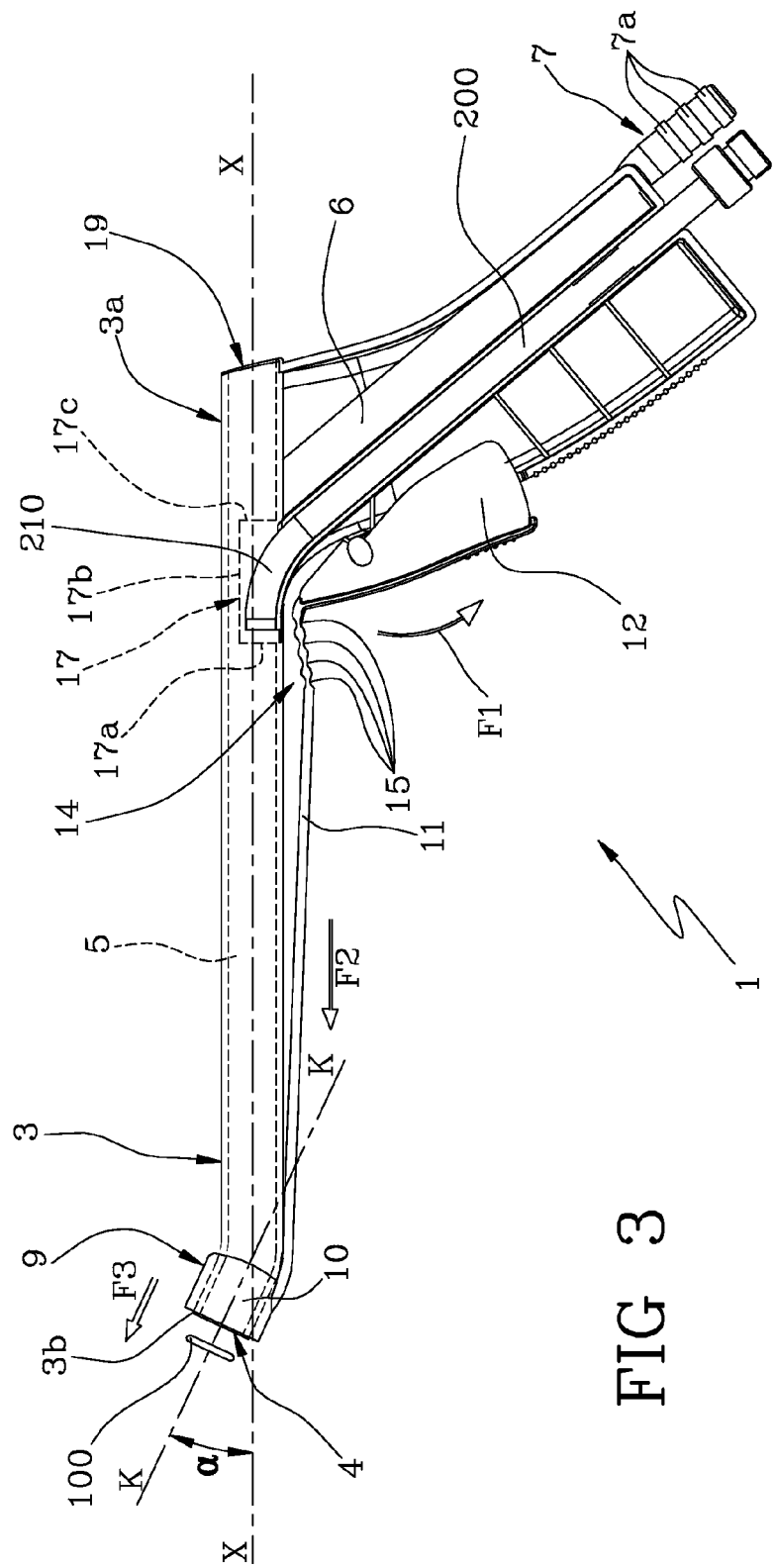
FIG. 3 is a lateral view in section of a device of FIG. 1.

In the figures of the drawings, 1 denotes in its entirety a device for elastic ligature of tissues such as, for example, the anal mucosa of a patient. The application is advantageously applied in treatment of hemorrhoidal complaints related to the mucosa.

The device 1 comprises a handle 2 for a user to grip, and further comprises an elongate first element 3, preferably tubular and having a circular section, destined together with the handle to give the device 1 an overall pistol confirmation.

The first element 3 exhibits a proximal end 3a, arranged at the handle 2, and a distal end 3b provided with a frontal opening 4.

The first element 3 internally exhibits a chamber 5 which extends substantially along the whole development of the first element 3 and which is in communication with the frontal opening 4.

The chamber 5 exhibits, opposite to the frontal opening 4, a rear opening 19 located at the distal end 3b.

The chamber 5 is further connectable to a pneumatic aspiration source, not illustrated, by means of as aspirating conduit 6 realized internally of the handle 2 and equipped with a connecting terminal 7. The connection terminal 7 exhibits surface reliefs 7a for improving a coupling with a connecting tube with a pneumatic aspiration source. By means of the action of the pneumatic aspiration transmitted by the aspiration conduit, and in combination with the closing of the rear opening 16 by the operator, a desired quantity of mucosa can be drawn through the frontal opening 4 internally of the chamber 5.

At the distal end 3b the first element 3 exhibits a support portion 8 for one or more rubber rings 100. The support portion 8 is preferably defined by a portion of the external surface of the first element 3.

The device 1 further comprises a second element 9 predisposed on the first element 3 such that the two elements 3, 9 are slidably coupled along the inclined direction K-K, which is inclined with respect to a prevalent development direction X-X of the first element 3.

The second element 9 comprises an active portion 10, which is substantially tubular and keyed on the first element 3 in order to slide along the inclined direction K-K.

The inclined direction K-K in which the element 9 slides defines, together with the prevalent development direction X-X of the first element 3, an angle α comprised between 0 and 30 degrees, preferably 25 degrees.

The second element further comprises an elongate connecting rod 11 developing substantially along the prevalent development direction X-X of the first element 3. The connecting rod 11 is fixed at an end thereof to the active portion 10.

The device 1 comprises a trigger 12 hinged to a frontal portion of the handle 2 such as to rotate about a hinge axis Y. In particular, as illustrated in FIG. 2, the handle 3 exhibits a cylindrical portion 13 snap-fittable to a corresponding cylindrical seating of the trigger 12. The snap-fit coupling is is done by reciprocal nearing between the trigger 12 and the handle 3 along a substantially parallel direction to the prevalent development direction X-X of the element 3.

The trigger 12 acts on the second element 9 to realize a translation of the second element 9 following a rotation of the trigger 12 about the hinge axis Y.

In particular, the trigger 12 causes an axial sliding of the connecting rod 11 with respect to the first element 3 when the trigger 12 is pressed by the user.

The sliding is done parallel to the prevalent direction X-X of the first element 3.

The sliding of the connecting rod 11 contemporaneously causes an advancement of the second element 9 towards the distal end 3b of the first element 3.

The advancement is done along the inclined direction K-K. The advancement of the second element 9 causes release of an elastic ring 100 from the support portion 8.

The device 1 advantageously comprises a flexible connecting portion 14, which in particular is elastically deformable and is active between the trigger 12 and the second element 9 in order to enable a variation in the reciprocal orientation between the trigger 12 and the second element 9.

The connecting portion 14 is fixed to the trigger 12 in an upper position of the trigger 12, i.e. a portion of the trigger 12 which is closer to the first element 3.

The connecting portion 14 comprises a strip having one or more reductions of thickness 15 defining pre-weakened zones, i.e. zones having a lesser flexional rigidity and destined to make the strip itself more elastically deformable. In the accompanying figures the strip exhibits a plurality of reductions of thickness 15 which give the connecting portion 14 an undulating conformation, i.e. a variable thickness alternating along the connection portion 14 itself.

In particular, the connecting portion 14 is fixed at a side thereof directly to the trigger 12, and at another side thereof to an end of the connecting rod 11 (the other end of the connecting rod 11 is connected to the active portion 10, as previously described). As the connecting portion is fixed to the trigger 12 at an upper portion of the trigger 12, the connecting rod 11 can remain adjacent to the first element 3, giving the device 1 a compact structure.

The connecting portion 14 preferably exhibits a compressive rigidity which is sufficient to determine a movement of the second element 9 slidingly with respect to the first element 3, while it exhibits a flexional rigidity which is sufficiently small to enable the connecting portion 14 to absorb dealignment between the trigger 12 and the second element 9. The dealignments between the trigger 12 and the second element 9 are due to the fact that the trigger 12, as it rotates, lowers the point of application of the thrust on the connecting portion 14 with respect to the second element 9.

The trigger 12 and the connecting portion 14 define command means of the reciprocal movement of the first element 3 and the second element 9.

The connecting portion 14 is advantageously made in a single piece with the second element 9 and the trigger 12. In other words, these three elements are made in a single element, made for example of plastic material by means of an industrial injection molding process.

Figure 4:
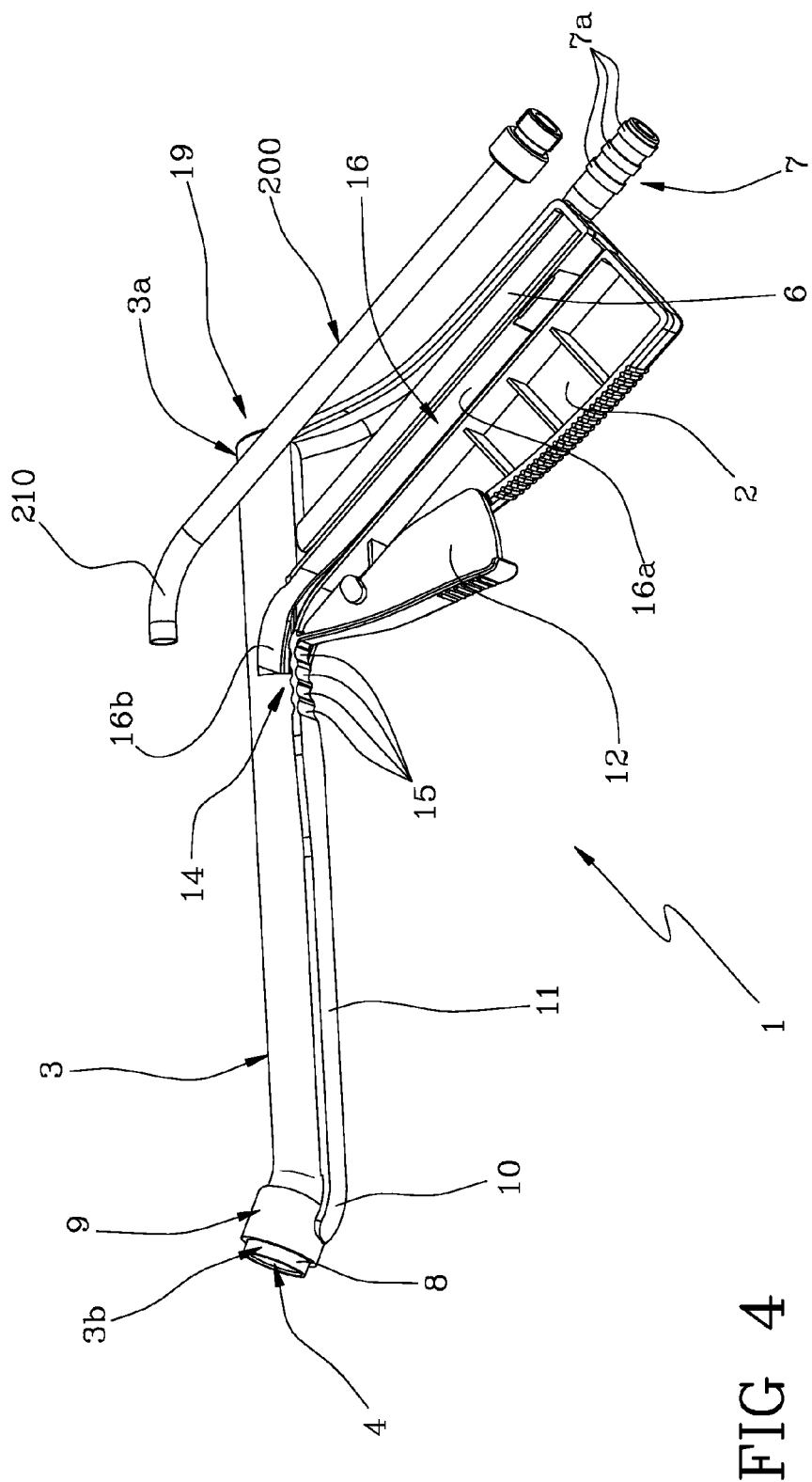
FIG. 4 is a perspective view of the device of FIG. 1.

As can be seen in FIG. 4, the handle 2 laterally exhibits a seating 16 for housing a light source, for example an optic fiber 200. The optic fiber 200 has a tubular conformation and exhibits a prevalent development direction.

The optic fiber 200 further exhibits an active end 210 for issuing a light beam, and the active end 210 is curved, i.e. it deviates from the prevalent development direction of the optic fiber 200 itself.

The seating 16 has a substantially complementary shape to the optic fiber 200, and in particular exhibits. a straight first portion 16a and a curved second portion 16b, which second portion is destined to house the active end 210 of the optic fiber 200.

The seating 16 is couplable with the optic fiber 200 in a reciprocal nearing movement along a perpendicular direction to the prevalent development direction of the seating 16. To this end, the seating 16 is laterally open.

Further, the seating 16 preferably exhibits snap-fit retaining means 18 for stably retaining the optic fiber 200 in the seating 16. The snap-fit retaining means 18 preferably comprise at least a pair of opposite projection able to elastically deform and enable a press-insertion of the optic fiber 200 in the seating 16, and a following stable retaining of the optic fiber 200 in the seating 16.

As can be seen in FIGS. 1 and 3, the first element 3 exhibits, internally thereof, a wall 17 which extends internally of the chamber 5 and which is in contact at one side with the chamber 5 and therefore with the pneumatic aspiration, and on the other side with the seating 16, and in particular with the curved second portion 16b of the seating 16. The wall 17 thus determines a separation of the seating 16 from the chamber 5.

The wall 17 preferably comprises a first tract 17a which extends transversally, preferably perpendicular, to the prevalent development direction X-X of the first element 3. The orientation of the first tract 17a of the wall 17 enables the active end 210 of the wall 17 enables the active end 210 of the optic fiber 200 to direct a light beam parallel to the prevalent development direction X-X of the first element 3 and towards the frontal opening 4.

In this configuration, the active end 210 of the optic fiber 200 extends internally of the tubular volume of the first element 3 but is separated from the pneumatic aspiration thanks to the wall 17. In this way contamination of the optic fiber 200 is avoided, and can be re-used.

The wall 17, which defines a sealed separation between the chamber 5 and the seating 16, exhibits further tracts 17b, 17c, defining a closure of the second portion 17b of the seating 17. In the illustrated embodiment, the wall 17 exhibits a substantially upturned-U conformation.

The seating 16 is preferably frontally arranged with respect to the aspiration conduit 6, i.e. in an intermediate position between the aspiration conduit 6 and the frontal opening 4. The active end 210 of the optic fiber 200 can this be in a closer position to the frontal opening 4 such as to realize an efficient illuminating action.

In a further embodiment, not illustrated, the trigger 12 and the connecting portion 14 can be solidly constrained to the first element 3 (internal) while the second element (external) is fixed to the handle 2.

The device is entirely made of a plastic material, preferably polycarbonate.

Further, preferably the device is entirely realized via an industrial injection molding process.

The device 1 functions as follows.

The device is arranged in such a position as to place the distal end 3b of the first element 3 is a position facing a portion of the mucous membrane, for example the anal mucosa.

The pneumatic aspiration is then activated and, by closing the rear opening 16, a depression is transmitted into the chamber to draw a portion of the mucosa internally of the chamber 5 through the frontal opening 4. The aspiration can be reduced or halted when a sufficient quantity of mucous membrane has been drawn into the chamber 5 through the opening and the rear opening 16 can be closed, which the operator performs by applying a finger thereto.

The device 1 is equipped with at least a rubber ring 100 which is stretched about the support portion 8. The positioning of the rubber ring 100 on the support portion 8 can be realized by a mounting cone of a substantially known type and therefore not illustrated.

Then, starting from the configuration of FIG. 1, in which a rubber ring 100 is arranged on the support surface 8, the trigger 12 is activated by pressure exerted by a user's finger and consequently the trigger 12 rotates about the hinge axis Y (the arrow F1 in FIG. 3). The pressure is in particular exerted in the rear part of the trigger 12, i.e. on the opposite side of the connecting portion 14 with respect to the hinge axis Y.

The rotation of the trigger 12 generates a thrust on the connecting portion 14 which causes the connecting portion 11 to slide with respect to the first element (arrow F2 of FIG. 4) and at the same time advances the active portion 10 of the second element 9 with respect to the first element 3 (arrow F3 of FIG. 4), pushing the rubber ring 100 beyond the support surface 8 and thus releasing the rubber ring 100 onto the portion of mucosa.

The rubber ring 100, by its elastic recall effect, closes, gripping a part of the mucosa and interrupting the blood flow to the portion of mucosa connected thereto and still present in the chamber 5.

The elastic deformability of the connecting portion 14 enables an automatic recall of the trigger 12 and the second element 9 into the initial position of FIG. 1. The device 1 can then be retracted for a new application on the same patient (and in this case it is preferable that at least a further rubber ring has been predisposed on the support portion 8).

The device 1 is of the single-use type, i.e. it is packed in a sterile environment and can be used on a single patient, and must be discarded after use.

The invention thus attains the set aims, and obviates any drawbacks noted in the prior art.

The device exhibits notable constructional simplicity which translates into low production and assembly costs. The device can in fact be made of only two components, the handle solidly constrained to the first element and the trigger solidly constrained to the connecting portion and the second element.

Assembly is extremely simple, and merely requires nearing the two components along the prevalent reciprocal sliding direction between the first element and the second element. This enables reciprocal engaging between the first element and the second element, and at the same time enables a snap-fitting of the trigger on the handle.

What is claimed is:

1. A device for elastic ligature of tissues, comprising:
a first and a second element, one of which exhibits a support portion configured to support at least a rubber band, the elements being slidably coupled to one another such that a reciprocal sliding between the elements determines a release of a rubber band from the support portion;
command means, manually maneuverable by an operator and acting on at least the second element for realizing a reciprocal sliding between the elements, the command means comprising a trigger which is activatable by an operator's finger;
wherein the command means further comprise a connecting portion, connected to the trigger and to the second element and being elastically deformable in order to enable a reciprocal change of orientation between the trigger and the second element, the second element being arranged externally of the first element, the device further comprising a gripping handle to which the trigger is rotatably applied and to which the first element is fixed, wherein the trigger is rotatably applied to the gripping handle by means of a snap-fit coupling realizable by a nearing movement of the trigger to the gripping handle along a substantially parallel direction to a reciprocal sliding direction of the first element and the second element.

2. The device of claim 1, wherein the second element, the trigger and the connecting portion are realized in a single piece.

3. The device of claim 1, wherein the connecting portion exhibits one or more thinner portions defining pre-weakened zones destined to afford the connecting portion elastically-deformable properties.

4. The device of claim 1, wherein the second element exhibits an active portion keyed on the first element and a connecting rod fixed on a side thereof to the active portion and on another side thereof to the connecting portion.

5. The device of claim 1, wherein the gripping handle exhibits a lateral seating, having a prevalent direction of development, for housing a light source, the seating being couplable with the light source in a reciprocal nearing movement along a direction which is perpendicular to the prevalent direction of development.

6. The device of claim 5, wherein the seating is laterally open and exhibits snap-action retaining means for stably retaining the light source in the seating.

7. The device of claim 5, wherein the first element internally exhibits a chamber which is connectable to means for generating pneumatic aspiration, and further exhibits a rear opening and a front opening, the front opening being destined to aspirate a portion of mucous membrane internally of the chamber by action of the pneumatic aspiration and a closure of the rear opening; the second element internally exhibiting a wall in contact on a side thereof with the chamber and on another side thereof with an end portion of the seating, and conformed such as to enable the end portion of the seating to extend internally of the first element in order to enable the light source to direct a light beam towards the front opening.

8. The device of claim 1, wherein the first element and the second element exhibit respective tubular portions, one of which exhibits the support portion.

* * * * *